(12) United States Patent
Yokoyama et al.

(10) Patent No.: US 11,300,552 B2
(45) Date of Patent: Apr. 12, 2022

(54) NITRIC OXIDE DETECTION DEVICE WITH REDUCING GAS

(71) Applicants: CAIRE Diagnostics Inc., Pleasanton, CA (US); NGK Spark Plug Co., Ltd., Nagoya (JP)

(72) Inventors: Takahiro Yokoyama, Komaki (JP); Tatsunori Ito, Inazawa (JP); Hiroyuki Nishiyama, Konan (JP); Masahiro Takakura, Komaki (JP); Shigeya Aoyama, Komaki (JP); Ryan R. Leard, Oakland, CA (US); David Anvar, Sunnyvale, CA (US); Solomon Ssenyange, Fremont, CA (US)

(73) Assignees: CAIRE Diagnostics Inc., Pleasanton, CA (US); NGK Spark Plug Co., Ltd., Nagoya (JP)

( * ) Notice: Subject to any disclaimer, the term of this patent is extended or adjusted under 35 U.S.C. 154(b) by 622 days.

(21) Appl. No.: 15/908,290

(22) Filed: Feb. 28, 2018

(65) Prior Publication Data
US 2018/0252690 A1   Sep. 6, 2018

Related U.S. Application Data

(60) Provisional application No. 62/465,370, filed on Mar. 1, 2017.

(51) Int. Cl.
*G01N 33/00* (2006.01)
*A61B 5/08* (2006.01)
(Continued)

(52) U.S. Cl.
CPC ......... *G01N 33/0037* (2013.01); *A61B 5/082* (2013.01); *A61M 16/10* (2013.01);
(Continued)

(58) Field of Classification Search
CPC .. G01N 33/0037; G01N 33/497; A61B 5/082; A61B 5/097; A61M 16/10; A61M 2202/0275; Y02A 50/245
(Continued)

(56) References Cited

U.S. PATENT DOCUMENTS

| 4,812,648 A | 3/1989 | Perlman |
| 4,947,861 A | 8/1990 | Hamilton |

(Continued)

FOREIGN PATENT DOCUMENTS

| CN | 102469954 A | 5/2012 |
| CN | 102596030 A | 7/2012 |

(Continued)

OTHER PUBLICATIONS

Certificate of Correction for U.S. Pat. No. 6,866,637 (1 page).
(Continued)

*Primary Examiner* — Jacqueline Cheng
*Assistant Examiner* — Tho Q Tran

(57) ABSTRACT

A measurement system is disclosed that includes features for detecting the presence of nitric oxide from a gas sample, such as exhaled breath. The measurement system includes an assembly that introduces one or more reducing gases into a reactor-sensor assembly to help stabilize the sensor signal response and improve the performance of the assembly over time. Suitable reducing gases include hydrogen gas ($H_2$), carbon dioxide (CO), benzaldehyde, bisphenol A, and other similar compounds. The reducing gas may be introduced directly from one or more surrounding gases or through tubing or inline piping. The reducing gas may be generated from the liquid or solid forms.

15 Claims, 6 Drawing Sheets

(51) Int. Cl.
*A61M 16/10* (2006.01)
*A61B 5/097* (2006.01)
*G01N 33/497* (2006.01)

(52) U.S. Cl.
CPC ...... *A61B 5/097* (2013.01); *A61M 2202/0275* (2013.01); *G01N 33/497* (2013.01); *Y02A 50/20* (2018.01)

(58) Field of Classification Search
USPC ........................................................ 600/532
See application file for complete search history.

(56) References Cited

U.S. PATENT DOCUMENTS

| | | | |
|---|---|---|---|
| 4,956,073 | A | 9/1990 | Pribat et al. |
| 5,081,871 | A | 1/1992 | Glaser |
| 5,447,165 | A | 9/1995 | Gustafsson |
| 5,531,218 | A | 7/1996 | Krebs |
| 5,565,075 | A | 10/1996 | Davis et al. |
| 5,795,787 | A | 8/1998 | Silkoff et al. |
| 5,922,610 | A | 7/1999 | Alving et al. |
| 6,010,459 | A | 1/2000 | Silkoff et al. |
| 6,038,913 | A | 3/2000 | Gustafsson et al. |
| 6,099,480 | A | 8/2000 | Gustafsson |
| 6,468,222 | B1 | 10/2002 | Mault et al. |
| 6,475,158 | B1 | 11/2002 | Orr et al. |
| 6,612,306 | B1 | 9/2003 | Mault |
| 6,635,415 | B1 | 10/2003 | Bollinger |
| 6,723,056 | B1 | 4/2004 | Alving et al. |
| 6,733,463 | B2 | 5/2004 | Moilanen et al. |
| 6,764,591 | B1 | 7/2004 | Dutta et al. |
| 6,843,900 | B2 | 1/2005 | Dutta et al. |
| 6,866,637 | B2 | 3/2005 | George et al. |
| 7,014,692 | B2 | 3/2006 | Nilsson et al. |
| 7,045,359 | B2 | 5/2006 | Birks et al. |
| 7,108,659 | B2 | 9/2006 | Ross et al. |
| 7,270,638 | B2 | 9/2007 | Lundberg et al. |
| 7,352,465 | B2 | 4/2008 | Fay et al. |
| 7,427,269 | B2 | 9/2008 | George et al. |
| 7,611,613 | B2 | 11/2009 | Dutta et al. |
| 7,678,062 | B2 | 3/2010 | George et al. |
| 7,687,275 | B2 | 3/2010 | Burdinski |
| 7,694,547 | B2 | 4/2010 | Dutta et al. |
| 7,704,214 | B2 | 4/2010 | Abraham-Fuchs et al. |
| 7,814,777 | B2 | 10/2010 | Van Kesteren |
| 7,846,739 | B2 | 12/2010 | von Bahr et al. |
| 8,040,516 | B2 | 10/2011 | Van Kesteren et al. |
| 8,057,653 | B2 | 11/2011 | Dutta et al. |
| 8,109,128 | B2 | 2/2012 | Kalkman et al. |
| 8,144,675 | B1 | 3/2012 | Loc et al. |
| 8,176,915 | B2 | 5/2012 | Jaffe et al. |
| 8,322,190 | B2 | 12/2012 | Kalkman et al. |
| 8,425,428 | B2 | 4/2013 | Wood |
| 8,796,034 | B2 | 8/2014 | von Bahr et al. |
| 9,164,080 | B2 | 10/2015 | Dutta et al. |
| 2002/0185129 | A1 | 12/2002 | Fisher et al. |
| 2004/0018630 | A1* | 1/2004 | Birks ................ G01N 33/497 436/116 |
| 2004/0063210 | A1* | 4/2004 | Steichen ................ B01D 53/90 436/55 |
| 2006/0027465 | A1 | 2/2006 | Nair et al. |
| 2006/0153761 | A1* | 7/2006 | Bandl-Konrad ...... F01N 3/0842 423/239.1 |
| 2006/0195040 | A1 | 8/2006 | Nason et al. |
| 2007/0281362 | A1 | 12/2007 | Vink et al. |
| 2008/0077037 | A1 | 3/2008 | Gouma et al. |
| 2008/0261332 | A1 | 10/2008 | Burdinski |
| 2009/0128819 | A1 | 5/2009 | Van Kesteren et al. |
| 2009/0229345 | A1 | 9/2009 | Van Kesteren |
| 2009/0248961 | A1 | 10/2009 | Van Dijk et al. |
| 2009/0288474 | A1 | 11/2009 | Kalkman et al. |
| 2010/0011836 | A1 | 1/2010 | Kalkman et al. |
| 2010/0020326 | A1 | 1/2010 | Van Kesteren |
| 2010/0043526 | A1 | 2/2010 | Helwegen et al. |
| 2010/0045990 | A1 | 2/2010 | Van Kesteren et al. |
| 2010/0081955 | A1 | 4/2010 | Wood, Jr. et al. |
| 2010/0089121 | A1 | 4/2010 | Hemmingsson et al. |
| 2010/0106039 | A1 | 4/2010 | Abraham-Fuchs et al. |
| 2010/0121212 | A1 | 5/2010 | Carlsson et al. |
| 2010/0137733 | A1 | 6/2010 | Wang et al. |
| 2010/0268106 | A1 | 10/2010 | Johnson et al. |
| 2011/0009762 | A1 | 1/2011 | Eichler et al. |
| 2011/0035158 | A1 | 2/2011 | Banos et al. |
| 2011/0046497 | A1 | 2/2011 | Abraham-Fuchs et al. |
| 2011/0066060 | A1 | 3/2011 | von Bahr et al. |
| 2011/0077545 | A1 | 3/2011 | Eichler |
| 2011/0158939 | A1 | 10/2011 | Tepper et al. |
| 2011/0239735 | A1 | 10/2011 | Setayesh et al. |
| 2011/0277536 | A1 | 11/2011 | McFaul |
| 2012/0006102 | A1 | 1/2012 | Bryant et al. |
| 2012/0065535 | A1 | 3/2012 | Abraham-Fuchs et al. |
| 2012/0113241 | A1 | 5/2012 | Shieh et al. |
| 2012/0123288 | A1 | 5/2012 | Van Kesteren et al. |
| 2012/0203126 | A1 | 8/2012 | Kahlman et al. |
| 2012/0271188 | A1 | 10/2012 | Van Kesteren |
| 2012/0310104 | A1 | 12/2012 | Van Kesteren et al. |
| 2013/0219988 | A1 | 8/2013 | Dutta et al. |
| 2013/0219995 | A1 | 8/2013 | Dutta et al. |
| 2013/0327122 | A1 | 12/2013 | Dutta et al. |
| 2013/0344609 | A1 | 12/2013 | Mayer et al. |
| 2014/0278144 | A1 | 9/2014 | Risk et al. |
| 2015/0122002 | A1* | 5/2015 | Mackaldener ..... G01N 33/0037 73/114.71 |
| 2015/0136616 | A1 | 5/2015 | Friedrich |
| 2015/0240802 | A1* | 8/2015 | Guthrie ................ F04B 49/065 417/44.1 |
| 2015/0250408 | A1 | 9/2015 | Ssenyange et al. |
| 2015/0295562 | A1 | 10/2015 | Agarwal et al. |
| 2017/0065208 | A1 | 3/2017 | Furusaki et al. |
| 2017/0299543 | A1* | 4/2017 | Akasaka ............ G01N 27/4074 |
| 2018/0146886 | A1 | 5/2018 | Leard et al. |
| 2018/0252690 | A1 | 9/2018 | Yokoyama et al. |
| 2018/0271405 | A1 | 9/2018 | Leard et al. |
| 2018/0271406 | A1 | 9/2018 | Furusaki et al. |
| 2019/0015081 | A1 | 1/2019 | Ssenyange et al. |

FOREIGN PATENT DOCUMENTS

| | | |
|---|---|---|
| CN | 106163394 A | 11/2016 |
| DE | 202016003205 | 11/2016 |
| EP | 0903575 A1 | 3/1999 |
| EP | 0606351 B1 | 8/1999 |
| EP | 0724723 B1 | 4/2000 |
| EP | 1384069 B1 | 6/2006 |
| EP | 1439781 B1 | 6/2006 |
| EP | 1661514 B1 | 7/2008 |
| EP | 1836477 B1 | 6/2011 |
| EP | 2082214 B1 | 7/2011 |
| EP | 1883803 B1 | 6/2012 |
| EP | 2762880 A1 | 8/2014 |
| EP | 3113683 | 1/2017 |
| JP | H01-132956 | 2/1989 |
| JP | 2005538819 A | 12/2005 |
| JP | 2006133039 A | 5/2006 |
| JP | 2009533682 A | 9/2009 |
| JP | 2017515614 A | 6/2017 |
| RU | 2143689 C1 | 12/1999 |
| RU | 2016136114 A | 4/2018 |
| WO | WO2004023997 A1 | 3/2004 |
| WO | WO2005088289 A1 | 9/2005 |
| WO | WO2006054114 A1 | 5/2006 |
| WO | WO2006072867 A1 | 7/2006 |
| WO | WO2006092751 A1 | 9/2006 |
| WO | WO2006114766 A2 | 11/2006 |
| WO | WO2007029164 A2 | 3/2007 |
| WO | WO2007120780 A2 | 10/2007 |
| WO | WO2008026146 A1 | 3/2008 |
| WO | WO2008026183 A1 | 3/2008 |
| WO | WO2008026189 A1 | 3/2008 |
| WO | WO2008052104 A2 | 5/2008 |
| WO | WO2008056307 A1 | 5/2008 |
| WO | WO2008056312 A1 | 5/2008 |
| WO | WO2008144433 A1 | 11/2008 |

(56) References Cited

FOREIGN PATENT DOCUMENTS

| WO | WO2009144628 A1 | 12/2009 |
|---|---|---|
| WO | WO2010070544 A1 | 6/2010 |
| WO | WO2011013046 A1 | 2/2011 |
| WO | WO2011048536 A1 | 4/2011 |
| WO | WO2011055286 A1 | 5/2011 |
| WO | WO2011101776 A1 | 8/2011 |
| WO | WO2012059835 A1 | 5/2012 |
| WO | WO2012135655 A1 | 10/2012 |
| WO | WO2013003429 A1 | 1/2013 |
| WO | WO2015134390 A1 | 9/2015 |
| WO | WO2015134895 A1 | 9/2015 |
| WO | WO2017095475 A1 | 6/2017 |
| WO | WO2018017502 A1 | 1/2018 |
| WO | WO2018098483 A1 | 5/2018 |
| WO | WO2018160733 A1 | 9/2018 |
| WO | WO2018183204 A1 | 10/2018 |
| WO | WO2018183215 A1 | 10/2018 |
| WO | WO2019018121 A1 | 1/2019 |

OTHER PUBLICATIONS

Excerpts from file history for U.S. Appl. No. 11/903,135 (205 pages).
Excerpts from file history for U.S. Appl. No. 11/348,943 (231 pages).
Excerpts from file history for U.S. Appl. No. 12/242,887 (221 pages).
Excerpts from file history for U.S. Appl. No. 12/525,301 (256 pages).
Excerpts from file history for U.S. Appl. No. 12/594,573 (182 pages).
Excerpts from file history for U.S. Appl. No. 12/859,388 (265 pages).
Excerpts from File History for U.S. Appl. No. 12/947,096 (339 pages).
File History for European Patent Application No. EP08755591.8 (185 pages).
File History for European Patent No. 1075659 (219 pages).
File History for European Patent No. 1819274 (125 pages).
File History for Reexamination Request No. 90/008,309 (U.S. Pat. No. 6,010,459) (135 pages).
File History for U.S. Pat. No. 5,795,787 (357 pages).
File History for U.S. Pat. No. 5,922,610 (371 pages).
File History for U.S. Pat. No. 6,010,459 (450 pages).
File History for U.S. Pat. No. 6,038,913 (169 pages).
File History for U.S. Pat. No. 6,099,480 (127 pages).
File History for U.S. Pat. No. 6,723,056 (113 pages).
File History for U.S. Pat. No. 6,733,463 (107 pages).
File History for U.S. Pat. No. 7,014,692 (135 pages).
File History for U.S. Pat. No. 7,352,465 (197 pages).
File History for U.S. Pat. No. 7,846,739 (578 pages).
Logan Reserch Ltd., "LR2000 Series A New Generation of Mobile, Integrated, Clinical, Real-Time Nitric Oxide Gas Analysers," Instruction Manual (37 pages).
U.S. Appl. No. 60/904,450, entitled "A Robust High Temperature Semiconducting CO Sensor," Date of Deposit Mar. 1, 2007 (17 pages).
U.S. Appl. No. 61/604,752, entitled "Obtaining Selectivity in Gas Sensors via a Sensor Array System Composed of P and N Type Material" (20 pages).
International Search Report and Written Opinion for International Application No. PCT/US 2015/019226, dated Aug. 14, 2015 (16 pages).
Patent Cooperation Treaty: Notification Concerning Transmittal of International Preliminary Report on Patentability (Chapter I of the Patent Cooperation Treaty) for International application No. PCT/2015/019226, dated Sep. 22, 2016 (12 pages).
Patent Cooperation Treaty: First Notice Informing the Applicant of the Communication of the International Application (To Designated Offices Which Do Not Apply the 30 month Time Limited Under Article 22(1)) for International application No. PCT/20115/019226, dated Oct. 8, 2015 (1 Page).
U.S. Appl. No. 61/955,192 entitled "Total Respiratory Monitor" filed Mar. 18, 2014 (18 Pages).
U.S. Appl. No. 14/495,853 entitled "Respiratory Monitor" filed Sep. 24, 2014 (54 Pages).
Patent Cooperation Treaty: Notification of Transmittal of the International Search Report and the Written Opinion of the International Searching Authority, or the Declaration for International Application No. PCT.US2017/042459, dated Oct. 2, 2017 (14 Pages).
Pantalei Simone et al, "Improving sensing features of a nanocomposite PEDOT: PSS sensor for NO breath monitoring," Sensors and Actuator B: Chemical, Elsevier BV, vol. 179, Oct. 23, 2012, pp. 87-94.
Patent Cooperation Treaty: Notification of Transmittal of the International Search Report and the Written Opinion of the International Searching Authority, or the Declaration for International application No. PCT/2018/024396, dated Jul. 9, 2018 (14 pages).
PCT Notification of Transmittal of the International Search Report and the Written Opinion of the International Searching Authority, or the Declaration for International Application No. PCT/US2018/024373, dated Jul. 25, 2018 (15 pages).
B.J. Novak et al: "Exhaled methyl nitrate as a noninvasive marker of hyperglycemia in type 1 diabetes," Proceedings of the National Academy of Sciences, vol. 104, No. 40, Oct. 2, 2007, pp. 15613-15618.
David Smith et al: "Can volatile compounds in exhaled breath be used to monitor control in diabetes mellitus?", Journal of Breath Research, vol. 5, No. 2, Apr. 21, 2011, p. 022001.
Il-Doo Kim et al: "Exhaled Breath Sensors" In: "Nano Devices and Circuit Techniques for Low-Energy Applications and Energy Harvesting," 2015, Springer Netherlands, Dordrecht.
European Patent Office, Communication pursuant to Article 94(3) EPC for Patent Application No. 15 713 594.8-1657, dated Oct. 27, 2017 (4 pages).
Reply to examination report to the European Patent Office for Patent Application No. 15713594.8, dated Mar. 6, 2018 (15 pages).
European Patent Office, Communication pursuant to Article 94(3) EPC for Patent Application No. 15 713 594.8-1115, dated Jul. 13, 2018 (4 pages).
Japan Patent Office, Office Action for Application No. 2016-573705, drafted Jul. 13, 2018 (4 pages).
Federal Service for Intellectual Property, Request of substantive examination for Application No. 2016136114/14 (056690), dated Nov. 9, 2018 (8 pages).
China National Intellectual Property Administration, First Office Action Issued by China National Intellectual Property Administration for PRC (China) Patent Application No. 201580012268.X, dated Sep. 25, 2018 (10 pages).
USPTO Office Action dated Apr. 18, 2019 for U.S. Appl. No. 15/213,224 (44 Pages).
Derwent Abstract, CN202374269 U (2 pages).
Patent Cooperation Treaty: Notification of Transmittal of the International Search Report and the Written Opionion of the International Searching Authority, or the Declaration No. PCT/2018/020277, dated Jun. 11, 2018 (15 pages).
File History Excerpts from U.S. Appl. No. 14/495,853.
Patent Cooperation Treaty: Notification Concerning Transmittal of International Preliminary Report on Patentability (Chapter I of the Patent Cooperation Treaty) for International Application No. PCT/US2018/020277, dated Sep. 12, 2019 (10 pages).

\* cited by examiner

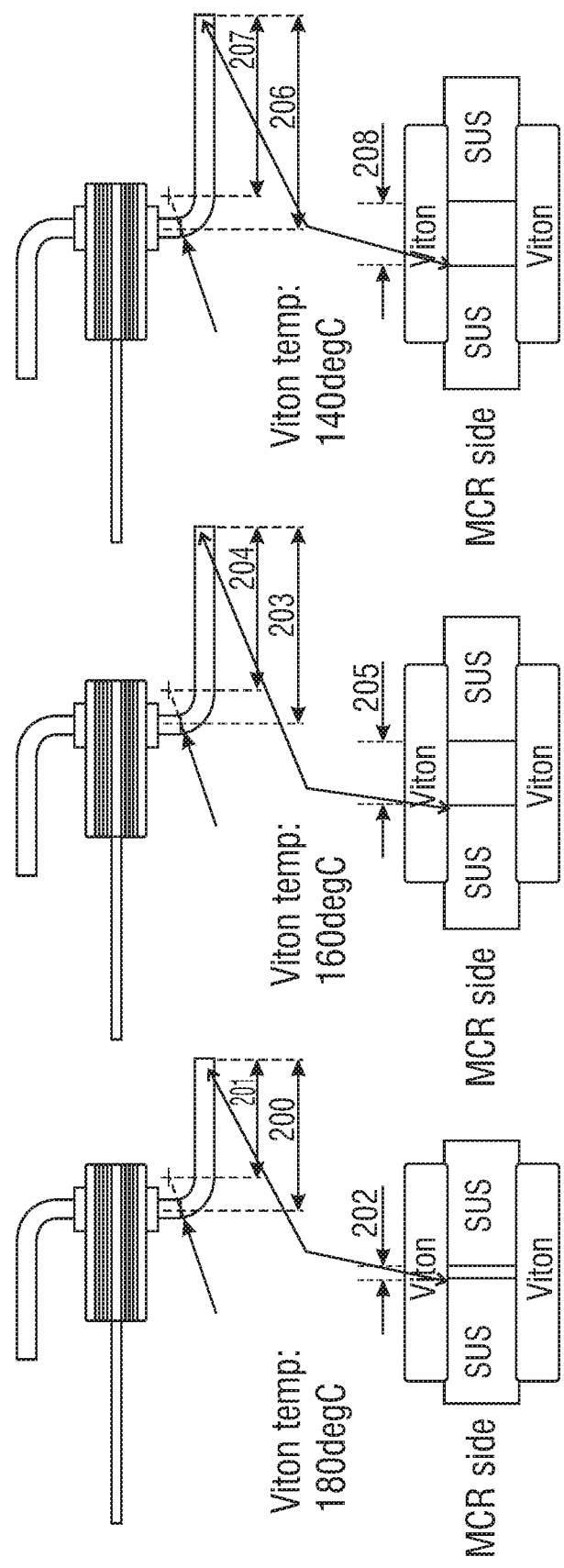

NITRIC OXIDE DETECTION DEVICE WITH REDUCING GAS

CROSS REFERENCE TO RELATED APPLICATIONS

This application claims the benefit of U.S. Provisional Application No. 62/465,370 filed on Mar. 1, 2017, the subject matter of which is herein incorporated by reference in its entirety.

FIELD OF THE INVENTION

The present invention relates generally to monitoring devices used to measure pulmonary functions, and more particularly to testing for nitric oxide, as well as other markers, associated with monitoring respiratory medical conditions.

BACKGROUND

Respiratory diseases are some of the most common disorders in the world. Such respiratory diseases include conditions such as chronic obstructive pulmonary disease (COPD), asthma, cystic fibrosis and pulmonary fibrosis. COPD, for example, affects millions of people and is responsible for extensive morbidity and mortality in the United States. COPD is a term used to describe chronic lung diseases characterized by progressive development of airflow limitation that is usually not fully reversible with medication. The common symptoms of COPD include breathlessness, wheezing and a chronic cough.

Asthma is another example of a chronic lung disease with symptoms similar to COPD, such as breathlessness and wheezing, but etiologically distinct from COPD. Asthma is a prevalent health care problem; it affects millions in the United States and around the world. A significant fraction of patients with asthma can be classified as having moderate to severe asthma and would benefit from more frequent monitoring of their airway inflammation. Although COPD and asthma require different treatments, test results for COPD and asthma often overlap.

Asthma in particular is characterized by an inflammatory reaction in hyper-reactive airways that restrict airflow into the lungs. In recent years, measurement of exhaled nitric oxide (eNO) has been shown to be a non-invasive and complementary tool to other pulmonary function tests in assessing airway inflammation, specifically in subjects with asthma. Accordingly, the presence of eNO has become a well-known, globally accepted biomarker for airway inflammation.

Nitric oxide (NO) is produced endogenously in cells by NO synthase and secreted by eosinophils in the distal alveoli. Its production is increased in response to inflammatory cytokines (which is associated with asthmatic episodes), and exhaled NO is thought to be an indirect measurement of airway eosinophilic inflammation. Thus, nitric oxide exhaled from the lower airways (e.g., non-nasal airways) can be correlated with the degree of airway inflammation. Patients with asthma have high levels of NO in their exhaled breath. Nitric oxide levels increase prior to the presence of clinical symptoms and its levels decline in response to appropriate therapy as airway inflammation subsides. These two characteristics make this an ideal biomarker for managing asthma status. For this reason, in 2011, the American Thoracic Society (ATS) issued new guidelines recommending the measurement of exhaled nitric oxide for the diagnosis and management of asthma. A diagnosis of asthma can be made when the level of nitric oxide in exhaled breath exceeds 50 ppb. High eNO levels are also associated with other inflammatory respiratory conditions.

In diagnosing respiratory diseases, a series of tests for eNO may be conducted. For example, point-of-care breath analyzers can provide eNO information to a physician or in a clinical setting, while handheld or portable breath analyzers can provide exhaled nitric oxide information to an individual patient. Details regarding respiratory monitors useful for the detection of eNO are described in U.S. Patent Publication No. 2015/0250408 A1, titled "Respiratory Monitor," the entirety of which is incorporated by reference herein. Details regarding additional respiratory monitors useful for the detection of eNO are described in U.S. Patent Publication No. 2017/0065208 A1, titled "Respiratory Monitor," the entirety of which is incorporated by reference herein. Respiratory monitoring devices using other sensors and other technologies also may test for various other biomarkers in a patient's breath.

An effective eNO test would be complimentary to the standard tests, but there is a dearth of inexpensive sensors capable of detecting the minute amounts of NO (typically measured in parts per billion) present in exhaled air. Moreover, NO sensors need to provide an accurate NO measurement in the presence of other possibly interfering gas components, including water and carbon dioxide ($CO_2$). A further challenge for NO measurement is the difficulty in distinguishing between NO and nitrogen dioxide ($NO_2$) in a patient's breath. That is, the gas introduced from the patient's breath typically has concentrations of NO, $NO_2$, $CO_2$, and oxygen ($O_2$). Traditional sensors are often unselective or incapable of distinguishing between the two main nitrogen oxides ($NO_x$) components of interest, NO and $NO_2$, resulting in erroneous readings.

Another challenge in current standard pulmonary function testing is ability to accurately and efficiently measure eNO for extended periods of time. For example, sensor response signals may deteriorate, provide inconsistent readings, and become unstable over time. This instability may render it more difficult to use the same sensor in a clinical setting and over different periods of time. The sensor also may require frequent replacement, which may increase the costs associated with maintenance and repair of the pulmonary function testing devices.

Thus, it would be desirable and advantageous to provide an accurate and efficient respiratory monitor capable of conducting multiple pulmonary function tests, as well as other associated measurements, that may be reliably used over extended periods of time. In some instances, it also may be desirable and advantageous to provide a respiratory monitor with a compact and portable footprint, useful in a variety of settings. Additionally, it would be desirable and advantageous to provide such measurement system with stabilized sensor response signals, thereby reducing maintenance and replacement costs.

BRIEF SUMMARY OF THE INVENTION

The present invention is generally directed to measurement systems for determining total nitrogen oxides ($NO_x$) concentration from a gas sample. Total $NO_x$ includes pure nitric oxide (NO), pure nitrogen dioxide ($NO_2$), and mixtures thereof. In one embodiment, a gas sample comprising $NO_x$ is directed through the gas flow pathway, through which the gas sample contacts a catalyst filter comprising platinum and a zeolite. The catalyst filter catalyzes the formation of an equilibrium mixture of NO and $NO_2$ from the gas sample comprising $NO_x$. The gas sample is exposed to a sensor having two electrodes on a solid electrolyte yttria-stabilized zirconia (YSZ). One electrode is a sensing potentiometric electrode. The other electrode is a reference potentiometric electrode. The sensor obtains the potential difference between the two electrodes. The total $NO_x$ content in the gas sample may be determined from the potential difference using a calibration curve. The use of one or more reducing gases in the measurement system helps to stabilize the sensor signal. It also may facilitate the extended use of the sensor in a respiratory monitor.

In some embodiments, a system for determining total $NO_x$, including NO and $NO_2$ concentrations in a gas stream is described. The system comprises a catalytic filter member, a sensor member positioned downstream from the catalytic filter, and a connection member disposed between the catalytic filter and sensor members. The catalytic filter member is adapted to catalyze the formation of an equilibrium mixture of NO and $NO_2$ from $NO_x$ in an incoming gas stream. The sensor member is adapted to contact the gas stream after the formation of the equilibrium mixture of NO and $NO_2$, and the sensor member is adapted to determine $NO_x$ concentration in the gas stream. The connection member is adapted to supply a reducing agent.

The reducing agent may be selected from the group consisting of hydrogen gas ($H_2$), carbon monoxide (CO), benzaldehyde, and bisphenol A. The reducing agent may comprise a reducing gas. The connection member may be adapted to promote reduction of oxygen ion ($O^{2-}$) at the sensor member so that oxidation of NO and $NO_2$ occurs substantially uninterrupted. The connection member may comprise fluoroelastomer tubing, Teflon tubing, stainless steel tubing, glass tubing, ceramic tubing, one or more canisters, or a combination thereof.

In preferred embodiments, the catalytic filter member comprises platinum-zeolite Y (PtY). The catalytic filter and sensor members are operated at different temperatures. The sensor member comprises a sensing potentiometric electrode adapted to contact the equilibrium mixture of NO and $NO_2$ and a reference potentiometric electrode disposed on an electrolyte substrate. The sensor member measures a potential difference between the two electrodes to obtain the $NO_x$ concentration in the gas stream. The system also may further comprise a controller in electrical communication with the sensor member. The controller determines total NO concentration in the gas stream based on the measured $NO_x$ concentration and the equilibrium mixture of NO and $NO_2$.

Also described is a system for determining total $NO_x$, including NO and $NO_2$ concentrations in a gas stream, comprising a catalytic filter member, a sensor member positioned downstream from the catalytic filter, and a connection member disposed between the catalytic filter and sensor members. The catalytic filter member is adapted to catalyze the formation of an equilibrium mixture of NO and $NO_2$ from $NO_x$ in an incoming gas stream. The sensor member is adapted to contact the gas stream after the formation of the equilibrium mixture of NO and $NO_2$ and determine $NO_x$ concentration in the gas stream. The connection member is adapted to promote reduction of oxygen ion ($O^{2-}$) at the sensor member so that oxidation of NO and $NO_2$ occurs substantially uninterrupted. In some embodiments, the connection member is adapted to promote substantially stable reduction of oxygen ion ($O^{2-}$) at the sensor member so that substantially stable oxidation of NO and $NO_2$ occurs substantially uninterrupted.

In addition, a measurement system for determining total $NO_x$, including NO and $NO_2$ concentrations in a gas stream comprises a gas flow pathway adapted to carry a gas stream comprising $NO_x$, a catalytic filter positioned in the gas flow pathway, a sensor positioned downstream from the catalytic filter, a connection member disposed between the catalytic filter and sensor, and a controller in electrical communication with the sensor. The catalytic filter comprises a platinum-zeolite Y (PtY) and is adapted to catalyze the formation of an equilibrium mixture of NO and $NO_2$ from $NO_x$ in the gas stream. The sensor is adapted to measure $NO_x$ concentration in the gas stream. The connection member is adapted to supply a reducing agent. The controller is adapted to determine total NO concentration in the gas stream based on the measured $NO_x$ concentration and the equilibrium mixture of NO and $NO_2$.

As is also described below, a measurement system for determining total $NO_x$, including NO and $NO_2$ concentrations in a gas stream comprises a gas flow pathway, a catalytic filter positioned in the gas flow pathway, a sensor positioned downstream from the catalytic filter, a connection member disposed between the catalytic filter and sensor, and a controller in electrical communication with the sensor. The catalytic filter comprises platinum-zeolite Y and is adapted to catalyze the formation of an equilibrium mixture of NO and $NO_2$ from $NO_x$ in the gas stream. The sensor is adapted to measure $NO_x$ concentration in the gas stream. The connection member is adapted to promote reduction of oxygen ion ($O^{2-}$) at the sensor so that oxidation of NO and $NO_2$ occurs substantially uninterrupted. The controller is adapted to determine total NO concentration in the gas stream based on the measured $NO_x$ concentration and the equilibrium mixture of NO and $NO_2$.

In another embodiment, a method is described for determining total $NO_x$, including NO and $NO_2$ concentrations in a gas sample. The method comprises the steps of flowing a gas sample comprising $NO_x$ through a gas flow pathway and exposing the gas sample to a catalytic filter positioned in the gas flow pathway. The catalytic filter comprises platinum-zeolite Y (PtY) and is adapted to catalyze the formation of an equilibrium mixture of NO and $NO_2$ from $NO_x$ in the gas sample. The method further comprises the step of exposing the gas sample to a sensor positioned in the gas flow pathway, downstream from the catalytic filter. The sensor is adapted to measure $NO_x$ concentration in the gas sample. The method also comprises the step of exposing the gas sample to a reducing agent after it has been exposed to the catalytic filter. The method further comprises the step of determining total NO concentration in the gas sample using a controller in electrical communication with the sensor. The controller determines total NO concentration based on the measured $NO_x$ concentration and the equilibrium mixture of NO and $NO_2$.

Additionally described is a method for determining total $NO_x$, including NO and $NO_2$ concentrations in a gas sample, comprising the steps of flowing a gas sample comprising $NO_x$ through a gas flow pathway and exposing the gas sample to a catalytic filter positioned in the gas flow pathway. The catalytic filter comprises platinum-zeolite Y (PtY) and is adapted to catalyze the formation of an equilibrium mixture of NO and $NO_2$ from $NO_x$ in the gas sample. The method further comprises the step of exposing the gas sample to a sensor positioned in the gas flow pathway, downstream from the catalytic filter. The sensor is adapted to measure $NO_x$ concentration in the gas sample. The method also comprises the step of exposing the gas sample to a connection member, thereby promoting reduction of oxygen ion ($O^{2-}$) at the sensor so that oxidation of NO and $NO_2$ occurs substantially uninterrupted. The method additionally comprises the step of determining total NO concentration in the gas sample using a controller in electrical communication with the sensor. The controller determines total NO concentration based on the measured $NO_x$ concentration and the equilibrium mixture of NO and $NO_2$.

BRIEF DESCRIPTION OF THE SEVERAL VIEWS OF THE DRAWINGS

FIG. 2A illustrates schematically conditions under which no reducing gas been introduced. FIG. 2B illustrates schematically conditions under which a reducing gas has been introduced.

FIGS. 6A through 6C illustrates schematically examples of portions of micro-channel reactor assemblies in accordance with various embodiments of the present invention. Fluoroelastomer tubing forms a connection between the micro-channel reactor and sensor units.

DETAILED DESCRIPTION OF THE INVENTION

As used herein, the terms "comprises," "comprising," "includes," "including," "has," "having," or any other variation thereof, are intended to cover a non-exclusive inclusion. For example, processes, methods, articles, or apparatuses that comprise a list of elements are not necessarily limited to only those elements but may include other elements not expressly listed or inherent to such processes, methods, articles, or apparatuses. Further, unless expressly stated to the contrary, "or" refers to an inclusive "or" but not to an exclusive "or." For example, a condition A or B is satisfied by any one of the following: A is true (or present) and B is false (or not present), A is false (or not present) and B is true (or present), and both A and B are true (or present).

Also, use of "a" or "an" are employed to describe the elements and components of the invention. This is done merely for convenience and to give a general sense of the invention. This description includes one or at least one and the singular also includes the plural unless it is obvious that it is meant otherwise.

Unless otherwise defined, technical and scientific terms used herein have the same meaning as commonly understood by one of ordinary skill in the art to which this invention belongs. Although methods that are similar or equivalent to those described herein can be used in the practice or testing of the present invention, suitable methods and materials are described herein. All publications, patent applications, patents, and other references mentioned herein are incorporated by reference in their entirety. In case of conflict, the present specification, including definitions, will control. In addition, materials, methods, and examples are illustrative only and not intended to be limiting.

In the following description, numerous specific details, such as the identification of various system components, are provided to understand the embodiments of the invention. One skilled in the art will recognize, however, that embodiments of the invention can be practiced without one or more of the specific details, ordinary methods, components, materials, etc. In still other instances, well-known structures, materials, or operations are not shown or described in detail to avoid obscuring aspects of various embodiments of the invention.

Reference throughout this specification to "one embodiment" or "an embodiment" means that a particular feature, structure, or characteristic described in connection with the embodiment is included in at least one embodiment of the present invention. Thus, the appearance of the phrases "in one embodiment" or "in an embodiment" in various places throughout this specification are not necessarily all referring to the same embodiment. Furthermore, the particular features, structures, or work characteristics may be combined in any suitable manner in one or more embodiments.

Figure 1:
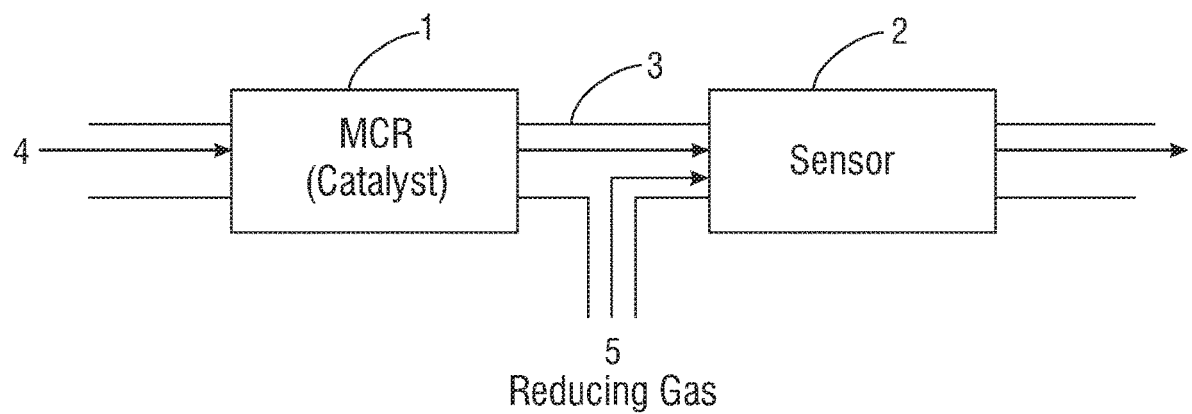
FIG. 1 illustrates schematically a top view of a micro-channel reactor and sensor assembly with the introduction of reducing gas at a junction between the reactor and sensor units, in accordance with one embodiment of the present invention.

Referring to FIG. 1, a schematic diagram of one embodiment of a reactor-sensor assembly used in the detection of nitric oxide (NO) is shown. The assembly includes a micro-channel reactor ("MCR") catalyst unit 1 and a sensor unit 2. The catalyst and sensor units communicate through one or more connectors 3. The connector may include, without limitation, one or more polymer tubes, piping, stainless steel tubing, or other gas conveying structures. Breath gas flows into the assembly from a flow path 4, first through the catalyst unit and then to the sensor unit, after which the breath gas is exhausted outside the device. In a preferred embodiment, the reactor and sensor assembly is composed of a stack of thin plates adhered together. The stacked configuration includes thin plates coated with catalytic material and sensor material. Spaces and openings between the various plates form channels to allow for gas flow through the assembly.

The reactor-sensor assembly is configured to determine the total NO concentration from the breath gas sample. A patient's breath sample can include nitrogen oxides ($NO_x$), which include pure NO, pure nitrogen dioxide ($NO_2$), and mixtures thereof. The gas introduced from the patient's breath typically has concentrations of NO, $NO_2$ and carbon monoxide (CO) in the range of 0 to 1000 ppb. Further, the gas typically contains 14-18% oxygen ($O_2$). In one embodiment, a micro-channel reactor and sensor assembly may include a catalyst filter comprising platinum and zeolite within the flow pathway. The catalytic filter and sensor are operated at different temperatures. The gas flowing through the flow pathway interacts with the catalyst filter at a particular temperature to form an equilibrium mixture of NO and $NO_2$. The micro-channel reactor and sensor assembly further includes a sensor element configured to sense the amount of $NO_x$ flowing therethrough.

In a preferred embodiment, the sensor element includes two electrodes on a solid yttria-stabilized zirconia ("YSZ") electrolyte substrate as follows: (1) a sensing potentiometric electrode disposed downstream of the catalytic filter device so as to contact the equilibrium mixture of NO and $NO_2$, and (2) a reference potentiometric electrode. A potential difference is obtained between the two electrodes, and the $NO_x$ concentration is ascertained by comparing the potential difference to a calibration curve. Because the relative amounts of NO and $NO_2$ are known due to the equilibrium reaction through the filter, the $NO_x$ reading of the sensor can be used to determine the amount of NO in the sample. Details regarding non-limiting examples of micro-channel reactor and sensor assemblies are described in U.S. Patent Publication Nos. 2015/0250408 A1 and 2017/0065208 A1, both titled "Respiratory Monitor," the entirety of which are incorporated by reference herein.

A reducing gas 5 may be introduced at the junction between the catalyst and sensor units. The reducing gas may be characterized by its ability to donate electrons and react with oxygen (e.g., from the YSZ electrolyte substrate), thus stabilizing the sensor response and facilitating extended use of the reactor-sensor assembly. The reducing gases may include, without limitation, the following gases: hydrogen gas ($H_2$), CO, benzaldehyde, bisphenol A, and the like. In this embodiment, the reducing gas is introduced at a T-junction in tubing, piping, or other gas conveying structure connecting the catalyst and sensor units. However, other structures, devices, and configurations of various shapes, sizes, and dimensions that are known in the art for conveying gases may be used to introduce the reducing gas.

Figure 2A:
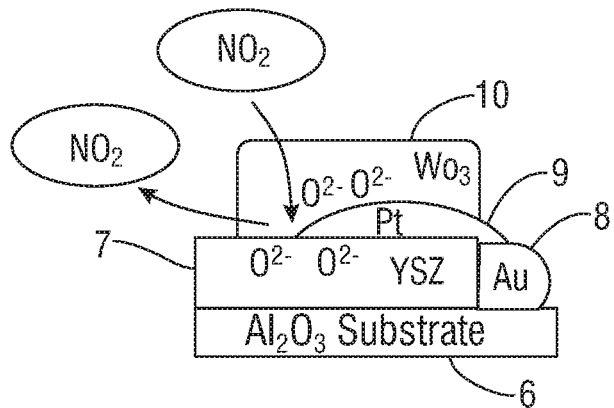
FIGS. 2A and 2B illustrate schematically cross-sectional side views of a sensor unit, in accordance with one embodiment of the present invention.
Figure 2B:
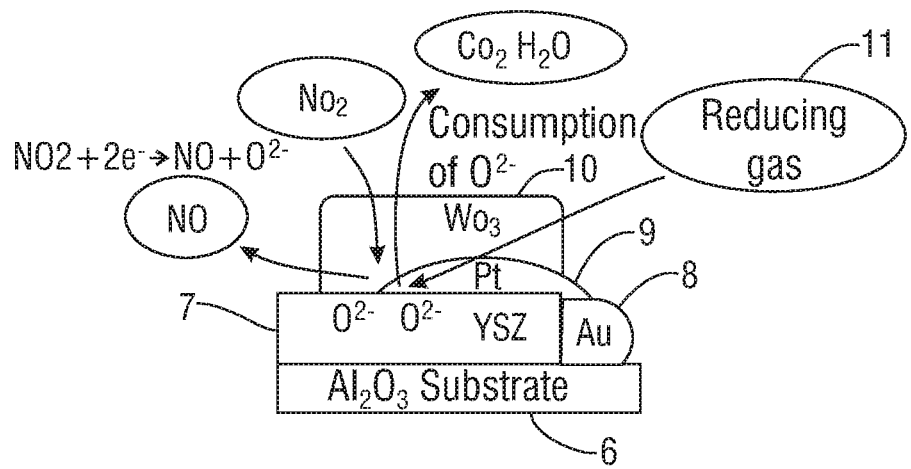

FIGS. 2A and 2B illustrate schematically portions of sensor units that include a catalyst filter comprising platinum and a zeolite, preferably platinum and zeolite Y (PtY), within the flow pathway. As shown in FIG. 2A, the sensor unit comprises an aluminum oxide ($Al_2O_3$) substrate 6 that includes the following layers: a solid YSZ electrolyte 7, gold (Au) 8, a platinum (Pt) counterelectrode 9, and a tungsten trioxide working electrode ($WO_3$) 10. Gas flowing through the sensor unit interacts with the catalyst filter to form an equilibrium mixture of NO and $NO_2$. It was found that in the absence of a reducing gas, available oxygen ($O^{2-}$) at the triple point boundary where the solid YSZ electrolyte 7, platinum 9, and tungsten trioxide 10 meet may hinder the production of NO.

As shown in FIG. 2B, a reducing gas 11 may be introduced into the flow pathway downstream from the catalytic reactor unit. When the reducing gas communicates with the sensor unit, the reducing gas reacts with oxygen ($O^{2-}$) at the triple point boundary where the solid YSZ electrolyte 7, platinum 9, and tungsten trioxide 10 meet to form carbon dioxide ($CO_2$), water ($H_2O$), or both. It will be appreciated that, in some embodiments, the sensor or sensor unit may include the micro-channel reactor catalyst-sensor assemblies and/or components described above.

The introduction of this reducing gas helps to consume oxygen at the sensor unit. In so doing, it helps to promote an oxygen defect at or near the triple point boundary that allows $NO_2$ from the breath gas sample to be reduced and thereby react with the remaining electrons to facilitate the formation of NO at the sensor unit. Specifically, the reducing agent helps to promote the reduction of the oxygen ion ($O^{2-}$) at the sensor element so that the oxidation of NO and $NO_2$ occurs substantially uninterrupted. In a preferred embodiment, the reducing agent helps to promote the substantially stable reduction of $O^{2-}$ at the sensor element so that the oxidation of NO and $NO_2$ occurs substantially uninterrupted. The introduction of the reducing gas and the resulting conversion of $NO_2$ to NO (e.g., generated from fluoroelastomer tubing, other tubing, other materials, or other substances in the gas, solid, or liquid form) may help to stabilize the sensor signal response, particularly as compared with the sensor signal response without the use of a reducing gas.

Figure 3:
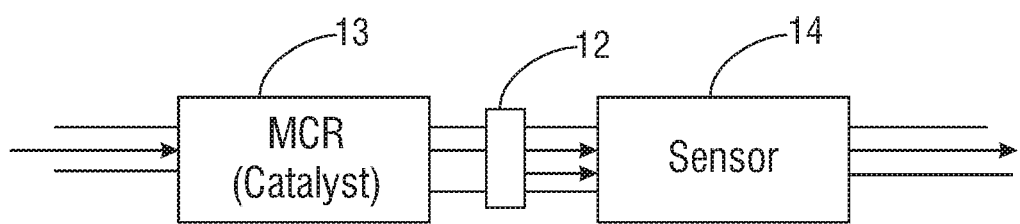
FIG. 3 illustrates schematically a top view of a micro-channel reactor and sensor assembly that includes inline tubing as a source of reducing gas, in accordance with one embodiment of the present invention. The inline tubing is positioned at a junction between the reactor and sensor units, and the inline tubing transmits reducing gas to the assembly.

Referring to FIG. 3, inline tubing 12, such as fluoroelastomer (Viton®), elastomer, polymer, rubber, or other tubing, may be positioned between the micro-channel reactor unit containing one or more catalysts 13 and the sensor unit 14. Here, the reducing gas is supplied from the inline tubing; however, as discussed, the reducing gas may be supplied by other structures, in other configurations, and in other forms. For example, the inside of the tubing may include a substance (e.g., a solid material) that may be heated to release a reducing gas. The reducing flows into the assembly through the tubing at the junction between the reactor and sensor units.

Figure 4A:
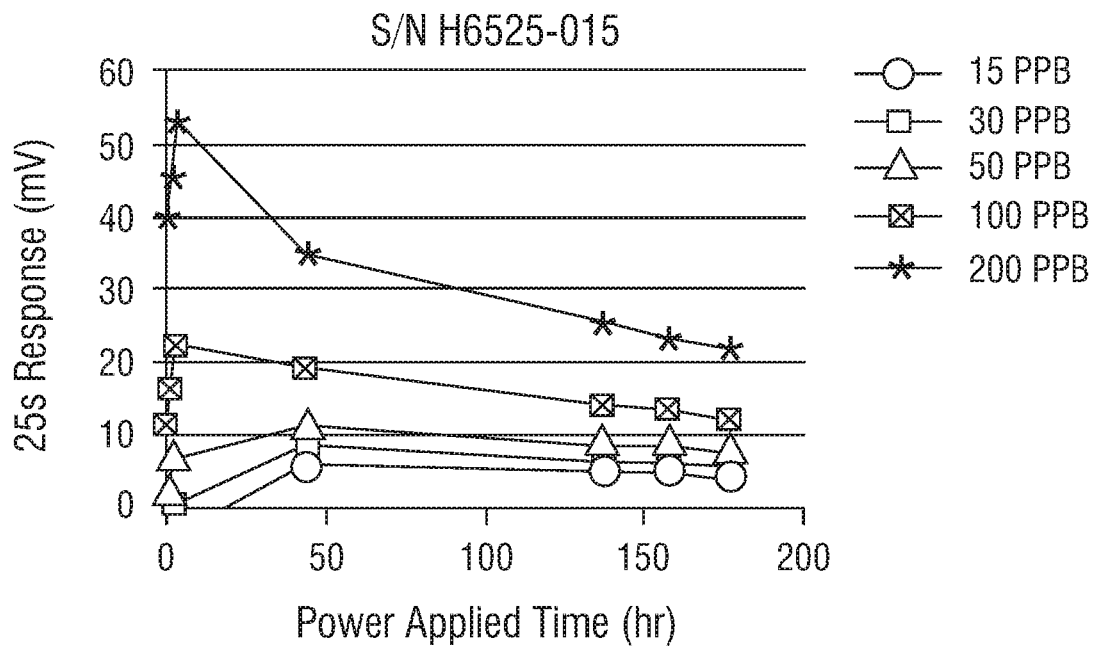
FIGS. 4A and 4B illustrate graphically examples of sensor responses for micro-channel reactor sensor assemblies using Teflon and fluoroelastomer tubing, respectively, according to one embodiment of the present invention. The sensor responses are depicted for breath gas samples containing NO concentrations ranging from 15 ppb to 200 ppb.
Figure 4B:
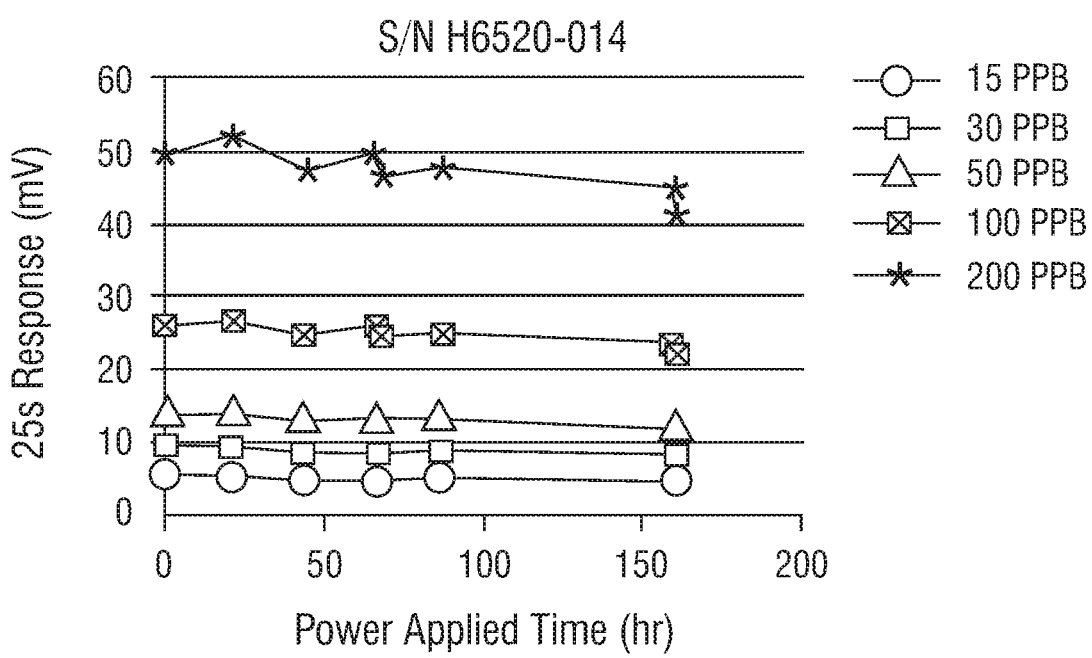

FIGS. 4A and 4B illustrate examples of micro-channel reactor sensor assembly ("MCRSH") characteristics in continuous operation where the reactor and sensor units are connected using Teflon tubing and fluoroelastomer (Viton®) tubing, respectively. In this example, the fluoroelastomer tubing supplied the reducing gas to the micro-channel reactor sensor assembly. The sensor units were evaluated by flowing 15-200 ppb of NO three times. The sensor unit was maintained at approximately 460° C., while the micro-channel reactor unit was maintained at approximately 320° C., with scrubber air flowing at a rate of 100 ccm. Each graph shows the 25 second response in mV as a function of the power applied time in hours, for gas samples with the different concentrations of NO.

As shown in the examples, the response for the assembly into which the reducing gas is introduced (FIG. 4B) was found to be relatively more stable with relatively smaller drops in sensitivity at least through approximately 150 hours than that for the assembly into which no reducing gas is introduced (FIG. 4A). Thus, the assembly that introduced the reducing gas may be more effectively used for a longer period of time without having to replace the sensor, as compared with the assembly that did not introduce the reducing gas. The results, signal responses, and measurement methods provided in this example are for illustrative purposes only. The use of the same, similar, or different reducing gases under different operating conditions may provide different response times over different period of time or using different measurement methods. For example, the use of a different reducing gas in a reactor-sensor assembly under different conditions may lead to more stable signals over time periods longer than those shown. Similarly, the use of the same reducing gas in a reactor-sensor assembly under different conditions may lead to more stable signals over time periods longer than those shown.

It also will be appreciated that one or more reducing gases may be introduced to the sensor reactor assembly using a variety of materials and methods known in the art that effectively allow for gas communication between the sensor and reactor units. As discussed above, one or more reducing gases may be introduced through the use of tubing, such as fluoroelastomer (Viton®), elastomer tubing, polymer, rubber, a composite, or other similar tubing.

The reducing gas also may be generated from other solid or liquid material that is heated, treated, or processed using other means to generate one or more reducing gases. A reducing gas may be introduced, for instance, from a solid or sponge-like material such as bisphenol A. In some embodiments, the bisphenol A material may be generated from a wide range of commercially available epoxy materials known in the art. Non-limiting examples of possible epoxy materials include Butylhydroxy Toluene from Epoxy EW2046 (commercially available as 3M™ Scotch-Weld™ Structural Adhesive EW2046), 2-Methyl-1-Benzofuran from Epoxy 2212B, Benzylamine from Epoxy XM5896T, and other similar materials through which bisphenol A may be generated.

Figure 5:
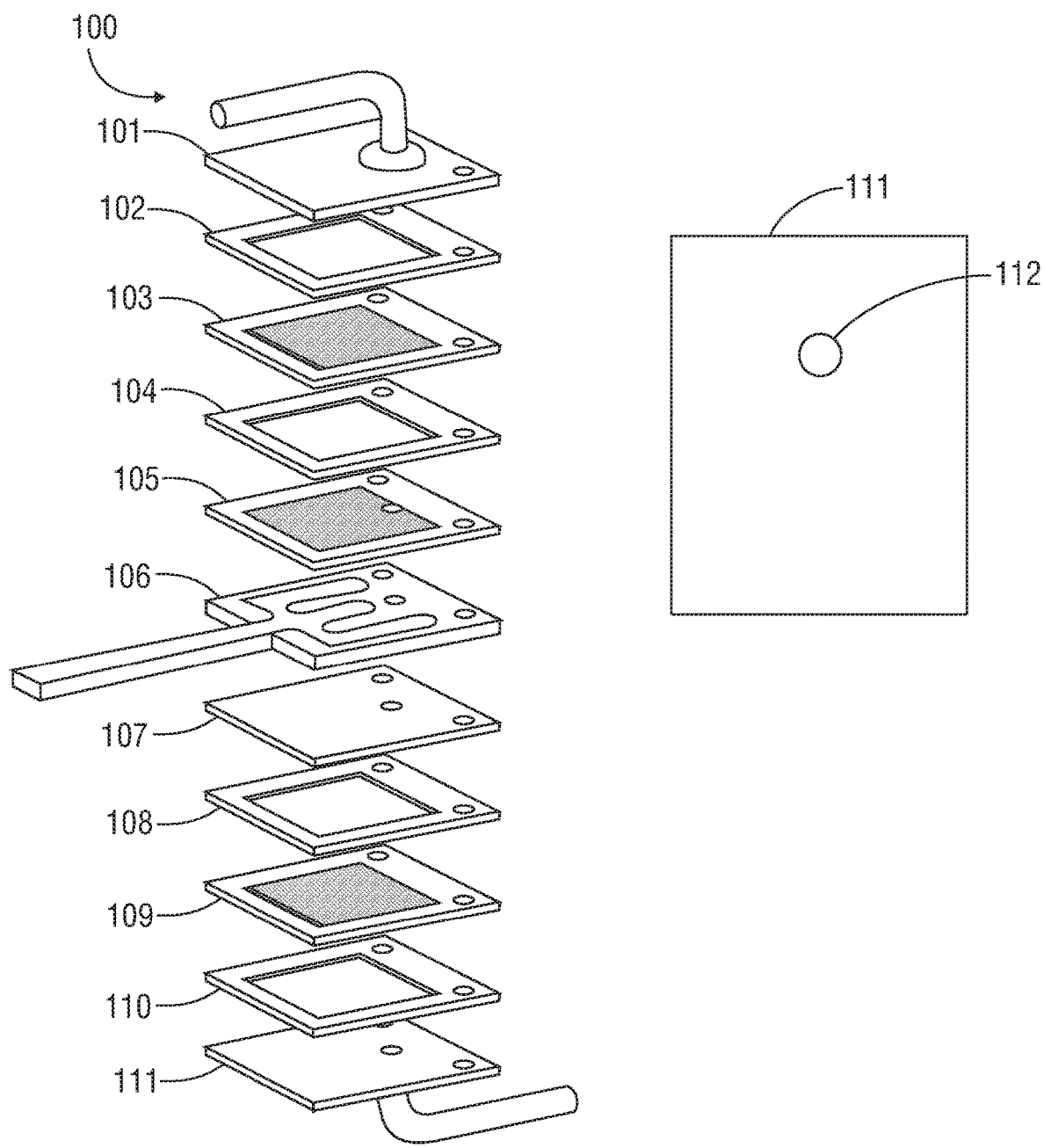
FIG. 5 illustrates schematically the application of epoxy material on a sensor plate to supply a reducing gas, in accordance with one embodiment of the present invention. In this embodiment, the epoxy is placed around a sensor plate opening through which the inlet tube will be placed.

Referring to FIG. 5, in one embodiment, an epoxy material may be applied on a portion of the sensor plate or an inlet adapter plate for a sensor unit. In this example, a microchannel reactor sensor assembly 100 includes an inlet adapter plate 101, spacer 102, PtY plate 103, spacer 104, PtY plate 105, a heater and resistance temperature detector (RTD) plate 106, sensor plate 107, spacer 108, PtY plate 109, another spacer 110, and an outlet adapter plate 111. An epoxy material may be applied around an opening 112 in the outlet adapter plate 111. In one embodiment, the epoxy material is heated and cured to allow for the generation of bisphenol A, which is then allowed to contact the sensor plate. In this embodiment, the breath sample can flow in through the inlet adaptor plate 101, down in the space provided between the plates that are coated with a catalytic material (here, PtY) along the gas path. The breath sample then passes up in a space provided between plates coated with a catalytic material before passing into yet another space provided between plates of the microchannel reactor/sensor assembly where the sensor resides and the breath sample can interact with the electrode materials on the surface of the sensor 107, pass the additional stacked plates shown, and exit ultimately through the outlet adaptor plate 111.

It will be appreciated that the amount of the reducing gas released into the gas flow path may be adjusted using a variety of methods known in the art for adjusting material flow. For example, the amount may be adjusted by changing the amount of material (such as epoxy) applied on the plate. The amount of the reducing gas also may be adjusted by changing the temperature and the temperature distribution across the sensor plate; i.e., around the inlet tube and at the center of the plate. In some embodiments, additional treatment of the material may help to stabilize the outgas amount.

In other embodiments, the reducing gas may be introduced between the micro-channel reactor and sensor units through the use of Teflon, stainless steel plates or tubing, glass tubing, ceramic, tubing, a combination of these materials, or other gas conveying apparatuses. For example, epoxy material may be placed within tubing placed between the reactor and sensor units and heated to supply bisphenol A as a reducing gas. In yet other embodiments, epoxy material may be placed outside the assembly, heated to generate bisphenol A, and fed into the assembly.

In other embodiments, the reducing gas of interest may be pumped, fed, or otherwise supplied directly in the gas form. For example, a gas containing the desired reducing component, such as $H_2$, CO, benzaldehyde, and bisphenol A, may be pumped from a canister or other container. As another example, air may be directed directly into the assembly through tubing, inline piping, canisters, other containers, or other structures known in the art for conveying gases. In some embodiments, the reducing gas may be obtained from a container, tubing, material, or other source that is permanently and irreplaceably configured with the reactor sensor assembly. In other embodiments, the reducing gas may be obtained from a container, tubing, material, or other source that is replaceable and removable from the reactor sensor assembly. The reducing gas may be obtained from one or more sources internal or external to the reactor sensor assembly.

The reducing gas, whether originally in gas, solid, liquid, or a combination of forms, may be conveyed to the reactor-sensor assembly through any known means or any combination of known means for conveying gases. The gas may be pumped in or through a tube or conveyed through mechanical means. As another non-limiting example, the gas may be introduced through a piezo-mechanical device that applies force to material to deliver the reducing gas. The gas may be generated and travel by diffusion, one or more chemical reactions, or other chemical means. The gas may also travel to the reactor-sensor assembly by absorption or desorption (e.g., heat transfer).

Further, the amount of the reducing gas may be adjusted by any known means for controlling gas flow rates. For example, the amount of reducing gas introduced into the gas flow path may be adjusted by controlling the flow rate of the gas using a pump or other device, or using other mechanical methods known in the art. In some embodiments, the amount of reducing gas available to react with the reactor sensor assembly may be determined by controlling the temperature or temperature range at which the gas is maintained. As discussed, the amount of the reducing gas introduced into the reactor sensor assembly also may be adjusted by controlling the amount of material used, as well as the curing, heat-treatment, or other processing conditions of the source material.

In some embodiments, the temperature and amount of the reducing gas may be controlled by adjusting the temperature at which the reducing gas is introduced. In some embodiments, the adjustments may be accomplished by adjusting the geometries within the reactor sensor assembly. In the examples shown in FIGS. 6A through 6C, a micro-channel reactor and sensor assembly includes fluoroelastomer (Viton®) tubing positioned between the steel plates at the micro-channel reactor side and the sensor side (not shown) of an assembly. The dimensions of the fluoroelastomer tubing (e.g., the exposed length of the tubing) may be varied to change the temperature of the tubing between the reactor and sensor units. In each of the assemblies, the sensor units are maintained at approximately 395° C., and the micro-channel reactor units are maintained at approximately 350° C.

In FIG. 6A, approximately 19.1 mm of fluoroelastomer tubing 200, measured from the stainless steel plate coupling (or approximately 14.9 mm measured from the edge of the assembly 201) was used. When the exposed length of the fluoroelastomer tubing 202 is less than approximately 0.3 mm, the temperature of the fluoroelastomer tubing is approximately 180° C. In FIG. 6B, a longer fluoroelastomer tubing 203 of approximately 25.1 mm, measured from the stainless steel plate coupling (or approximately 20.9 mm measured from the edge of the assembly 204) was used. When the exposed length of the fluoroelastomer tubing 205 was increased to approximately 1.0+/−0.2 mm, the temperature of the tubing decreased to approximately 160° C. In FIG. 6C, a longer fluoroelastomer tubing 206 of approximately 29.6 mm, measured from the stainless steel plate coupling (or approximately 25.4 mm measured from the edge of the assembly 207) was used. When the exposed length of the tubing 208 was approximately 1.0+/−0.2 mm, the temperature of the tubing decreased to approximately 140° C. As shown in these experiments, closer placement of the stainless steel plates between the reactor and sensor sides resulted in an increase in the temperature of the fluoroelastomer tubing that was positioned between the plates.

The present invention provides for the use of reducing gas to stabilize sensor signals in a wide variety of reactor sensor assemblies and for the detection of NO and other biomarkers. The reactor sensor assemblies may include dimensions, configurations, materials, components, assemblies, or catalysts different from those examples described in this application. For example, the use of a reducing gas may be used to stabilize sensor response signals in micro-channel reactor sensor assemblies, or other reactor-sensor assemblies, that include employ different catalysts, different sensors, or different plate configurations.

In addition, the measured stabilities, measurement methods, responses, sensitivities, times, durations, operating conditions, levels of effectiveness, materials, measurements, and methods described in the examples presented in this application are provided for illustration purposes only. It will be appreciated that the introduction of one or more reducing gases in accordance with the present invention may occur with different measured stabilities, measurement methods, responses, sensitivities, times, durations, operating conditions, levels of effectiveness, materials, measurements, and methods. For example, the reducing gas described in this application, or other reducing gases, may provide improved stability through longer or shorter periods of times and under different operating conditions.

As for additional details pertinent to the present invention, materials and manufacturing techniques may be employed as within the level of those with skill in the relevant art. The same may hold true with respect to method-based aspects of the invention in terms of additional acts commonly or logically employed. Also, it is contemplated that any optional feature of the inventive variations described may be set forth and claimed independently, or in combination with anyone or more of the features described herein. The breadth of the present invention is not to be limited by the subject specification, but rather only by the plain meaning of the claim terms employed.

This disclosure is sufficient to enable one of ordinary skill in the art to practice the invention, and provides the best mode of practicing the invention presently contemplated by the inventor. While a full and complete disclosure is made of specific embodiments of this invention, the invention is not limited by the exact construction, dimensional relationships, and operation shown and described. Various modifications, alternative constructions, design options, changes and equivalents will be readily apparent to those skilled in the art and may be employed, as suitable, without departing from the spirit and scope of the invention. Such changes might involve alternative materials, components, structural arrangements, sizes, shapes, forms, functions, operational features and the like.

What is claimed is:

1. An apparatus for determining total nitrogen oxides ($NO_x$), including nitric oxide (NO) and nitrogen dioxide ($NO_2$) concentrations in a gas stream, comprising:
    (a) a catalytic filter member adapted to catalyze the formation of an equilibrium mixture of NO and $NO_2$ from $NO_x$ in an incoming gas stream;
    (b) a sensor member positioned downstream from the catalytic filter member, wherein the sensor member is positioned on an electrolyte substrate comprising a charged portion, and further wherein the sensor member is adapted to determine total $NO_x$ concentration in the gas stream; and
    (c) a connection member disposed between the catalytic filter member and sensor member, wherein the connection member is configured to supply a reducing agent between the catalytic filter member and sensor member, wherein the reducing agent interacts with the charged portion of the electrolyte substrate to promote the formation of the equilibrium mixture of NO and $NO_2$, and further wherein the reducing agent comprises at least one of the following: hydrogen gas ($H_2$), carbon monoxide (CO), benzaldehyde, or bisphenol A.

2. The apparatus of claim 1, wherein the connection member comprises elastomer tubing.

3. The apparatus of claim 1, wherein the connection member is selected from the group consisting of Teflon tubing, stainless steel tubing, and elastomer tubing.

4. The apparatus of claim 1, wherein the reducing agent comprises a reducing gas.

5. An apparatus for determining total nitrogen oxides ($NO_x$), including nitric oxide (NO) and nitrogen dioxide ($NO_2$) concentrations in a gas stream, comprising:
    (a) a catalytic filter member adapted to catalyze the formation of an equilibrium mixture of NO and $NO_2$ from $NO_x$ in an incoming gas stream;
    (b) a sensor member positioned downstream from the catalytic filter member, the sensor member adapted to determine total $NO_x$ concentration in the gas stream; and
    (c) a connection member disposed between the catalytic filter member and sensor member, the connection member configured to supply a reducing agent between the catalytic filter member and sensor member, wherein the reducing agent comprises bisphenol A.

6. An apparatus for determining total nitrogen oxides ($NO_x$), including nitric oxide (NO) and nitrogen dioxide ($NO_2$) concentrations in a gas stream, comprising:
    (a) a gas flow pathway adapted to carry a gas stream comprising $NO_x$;
    (b) a catalytic filter positioned in the gas flow pathway, wherein the catalytic filter is adapted to catalyze the formation of an equilibrium mixture of NO and $NO_2$ from $NO_x$ in the gas stream;
    (c) a sensor positioned downstream from the catalytic filter, wherein the sensor is positioned on an electrolyte substrate comprising a charged portion, and further wherein the sensor is adapted to generate a response signal indicative of the concentration of $NO_x$ in the gas stream; and
    (d) a reducing element disposed between the catalytic filter and sensor, wherein the reducing element interacts with the charged portion of the electrolyte substrate to stabilize the sensor response signal, and further wherein the reducing element comprises bisphenol A.

7. An apparatus for determining total nitrogen oxides ($NO_x$), including nitric oxide (NO) and nitrogen dioxide ($NO_2$) concentrations in a gas stream, comprising:
    (a) a gas flow pathway adapted to carry a gas stream comprising $NO_x$;
    (b) a catalytic filter positioned in the gas flow pathway, wherein the catalytic filter is adapted to catalyze the formation of an equilibrium mixture of NO and $NO_2$ from $NO_x$ in the gas stream;
    (c) a sensor positioned downstream from the catalytic filter, wherein the sensor is positioned on an electrolyte substrate comprising a charged portion, and further wherein the sensor is adapted to generate a response signal indicative of the concentration of $NO_x$ in the gas stream; and (d) a reducing element disposed between the catalytic filter and sensor, wherein the reducing element interacts with the charged portion of the electrolyte substrate to stabilize the sensor response signal, and further wherein the reducing element is selected from the group consisting of hydrogen gas ($H_2$), carbon monoxide (CO), benzaldehyde, and bisphenol A.

8. A method for determining total nitrogen oxides ($NO_x$), including nitric oxide (NO) and nitrogen dioxide ($NO_2$) concentrations in a gas sample, comprising:
   (a) flowing the gas sample comprising $NO_x$ through a gas flow pathway;
   (b) flowing the gas sample to a catalytic filter member positioned in the gas flow pathway, wherein the catalytic filter member is adapted to catalyze the formation of an equilibrium mixture of NO and $NO_2$ from $NO_x$ in the gas sample;
   (c) flowing the gas sample to a sensor member after the gas sample has flowed to the catalytic filter member, wherein the sensor member is positioned on an electrolyte substrate and is adapted to measure total $NO_x$ concentration in the gas sample; and
   (d) contacting the gas sample with a reducing agent, wherein the reducing agent is supplied by a connection member in communication with the gas flow pathway at a location between the catalytic filter member and sensor member, wherein the reducing agent interacts with a charged portion of the electrolyte substrate to promote the formation of the equilibrium mixture of NO and $NO_2$, and further wherein the reducing agent comprises at least one of the following: hydrogen gas ($H_2$), carbon monoxide (CO), benzaldehyde, or bisphenol A.

9. The method of claim 8, wherein the connection member comprises elastomer tubing.

10. The method of claim 8, wherein the connection member is selected from the group consisting of Teflon tubing, stainless steel tubing, and elastomer tubing.

11. The method of claim 8, wherein the reducing agent comprises a reducing gas.

12. The method of claim 8, wherein the reducing agent is selected from the group consisting of hydrogen gas ($H_2$), carbon monoxide (CO), benzaldehyde, and bisphenol A.

13. A method for determining total nitrogen oxides ($NO_x$), including nitric oxide (NO) and nitrogen dioxide ($NO_2$) concentrations in a gas sample, comprising:
   (a) flowing the gas sample comprising $NO_x$ through a gas flow pathway;
   (b) flowing the gas sample to a catalytic filter member positioned in the gas flow pathway, wherein the catalytic filter member is adapted to catalyze the formation of an equilibrium mixture of NO and $NO_2$ from $NO_x$ in the gas sample;
   (c) flowing the gas sample to a sensor member positioned downstream from the catalytic filter member, the sensor member adapted to measure total $NO_x$ concentration in the gas sample; and
   (d) contacting the gas sample with a reducing agent, wherein the reducing agent is supplied by a connection member in communication with the gas flow pathway at a location between the catalytic filter member and sensor member, and further wherein the reducing agent comprises bisphenol A.

14. A method for determining total nitrogen oxides ($NO_x$) including nitric oxide (NO) and nitrogen dioxide ($NO_2$) concentrations in a gas sample, comprising:
   (a) catalyzing the formation of an equilibrium mixture of NO and $NO_2$ from $NO_x$ in the gas sample using a catalytic filter;
   (b) generating a response signal indicative of the $NO_x$ concentration in the gas sample using a sensor positioned on an electrolyte substrate downstream from the catalytic filter; and
   (c) stabilizing the sensor response signal using a reducing element disposed between the catalytic filter and sensor, wherein the reducing element interacts with a charged portion of the electrolyte substrate to stabilize the sensor response signal, and further wherein the reducing element comprises bisphenol A.

15. A method for determining total nitrogen oxides ($NO_x$) including nitric oxide (NO) and nitrogen dioxide ($NO_2$) concentrations in a gas sample, comprising:
   (a) catalyzing the formation of an equilibrium mixture of NO and $NO_2$ from $NO_x$ in the gas sample using a catalytic filter;
   (b) generating a response signal indicative of the $NO_x$ concentration in the gas sample using a sensor positioned on an electrolyte substrate downstream from the catalytic filter; and
   (c) stabilizing the sensor response signal using a reducing element disposed between the catalytic filter and sensor, wherein the reducing element interacts with a charged portion of the electrolyte substrate to stabilize the sensor response signal, and further wherein the reducing element is selected from the group consisting of hydrogen gas ($H_2$), carbon monoxide (CO), benzaldehyde, and bisphenol A.

\* \* \* \* \*